United States Patent
Finley

(10) Patent No.: US 8,652,518 B2
(45) Date of Patent: Feb. 18, 2014

(54) COMPOSITIONS AND METHODS FOR THE PREVENTION AND TREATMENT OF DISEASES OR CONDITIONS ASSOCIATED WITH OXIDATIVE STRESS, INFLAMMATION, AND METABOLIC DYSREGULATION

(76) Inventor: Jahahreeh Finley, Houston, TX (US)

( * ) Notice: Subject to any disclaimer, the term of this patent is extended or adjusted under 35 U.S.C. 154(b) by 13 days.

(21) Appl. No.: 13/447,243

(22) Filed: Apr. 15, 2012

(65) Prior Publication Data

US 2013/0273175 A1    Oct. 17, 2013

(51) Int. Cl.
*A61K 9/20* (2006.01)
*A61K 36/00* (2006.01)
*A61K 38/43* (2006.01)

(52) U.S. Cl.
USPC .......................... 424/464; 424/725; 424/94.1

(58) Field of Classification Search
USPC .......................... 424/725, 464, 94.1
See application file for complete search history.

(56) References Cited

U.S. PATENT DOCUMENTS

| 5,656,667 A | 8/1997 | Breivik et al. |
| 6,569,624 B1 | 5/2003 | Weindruch et al. |
| 6,660,297 B2 * | 12/2003 | Bartels et al. ................. 424/464 |
| 7,976,879 B2 * | 7/2011 | Roizen ........................... 424/725 |
| 2004/0001817 A1 * | 1/2004 | Giampapa .................... 424/94.1 |
| 2011/0070258 A1 | 3/2011 | Jimenez Del Rio et al. |

* cited by examiner

*Primary Examiner* — Blessing M Fubara
*Assistant Examiner* — Jennifer Berrios
(74) *Attorney, Agent, or Firm* — Jahahreeh Finley

(57) ABSTRACT

The present invention relates to methods and formulations for the prevention or treatment of diseases or conditions associated with oxidative stress, inflammation, and metabolic dysregulation. Specifically, the present invention comprises compositions and methods that increase mitochondrial biogenesis, alleviate inflammation, and increase the level of endogenous enzymatic and non-enzymatic antioxidants in a subject.

20 Claims, No Drawings

COMPOSITIONS AND METHODS FOR THE PREVENTION AND TREATMENT OF DISEASES OR CONDITIONS ASSOCIATED WITH OXIDATIVE STRESS, INFLAMMATION, AND METABOLIC DYSREGULATION

CROSS REFERENCE TO RELATED APPLICATIONS

Not Applicable

FIELD OF THE INVENTION

The present invention relates to methods and formulations for the prevention or treatment of diseases or conditions associated with oxidative stress, inflammation, and metabolic dysregulation in a subject utilizing phytochemicals, natural plant extracts, and pharmaceutical compositions. In a preferred embodiment, the present invention describes the combination of a topical beta-adrenergic receptor blocker, vitamins A, C, and E, zinc, selenium, lutein, copper, eicosapentaenoic acid (EPA), docosahexaenoic acid (DHA), acetylsalicylic acid (ASA), metformin, N-acetyl-L-cysteine (NAC), Coenzyme Q10 (CoQ10), melatonin, and magnesium.

BACKGROUND OF THE INVENTION

Although a linear definition of aging and its effects on diseases associated with oxidative stress, inflammation, and metabolic dysregulation has been elusive, the process of aging can be thought of as a stochastic process that systemically occurs in animals after reproductive maturity, resulting in a gradual increase in molecular disorder. As molecular fidelity decreases, the cell's ability to repair or replace molecular constituents becomes abrogated, leading to increased susceptibility to age-related diseases.

Interestingly, because aberrant cellular energetics (i.e. metabolic dysregulation) have been shown in several model organisms to determine lifespan and longevity, nearly all molecules, including those that orchestrate cellular repair and replacement, must be subject to the same stochastic process that potentiates molecular disorder and decreases fidelity. Indeed, such molecules must have existed at one point in time (before reproductive maturity) without any changes associated with the process of aging.

Thus, because aging is an imbalance between cellular damage and repair, researchers have focused on the etiological players of cellular damage and have highlighted three wide-ranging pathological states that have been associated with the origin of numerous age-related and non-age related disease states: (1) oxidative stress; (2) inflammation; and (3) metabolic dysregulation (i.e. mitochondrial dysfunction).

Oxidative Stress

Oxidative stress results in a pathological setting wherein an imbalance exists between the production of reactive oxygen species (ROS) and its destruction by enzymatic and nonezymatic endogenous and exogenous antioxidants (e.g. superoxide dismutase, catalase, peroxidases, gluathione, NADPH, thioredoxin, and vitamins C and E). ROS are highly reactive metabolites of molecular oxygen ($O_2$) and include nonradical as well as radical molecules such as hydrogen peroxide ($H_2O_2$) and hydroxyl ($\cdot OH$) and superoxide ($O_2-$) radicals, respectively.

ROS formation is a normal byproduct of aerobic metabolism and can be taken up from the external environment or produced in excess under pathological conditions (e.g. NADPH oxidase production of ROS in Alzheimer's disease). High levels of ROS can directly damage cellular constituents including lipids, protein, and DNA (along with a precipitous decline in antioxidant enzyme activity with increasing age) and have been shown to be a causal factor in a wide range of disorders such as diabetes, glaucoma, hearing loss, infertility, and Parkinson's disease.

Chronic Inflammation

A state of chronic, low-grade inflammation has been shown to play a central role in linking the aging process with the onset of age-related diseases. Essentially, the immune system becomes increasingly dysregulated as a function of age, primarily through an imbalance of the redox status, as discussed above. Indeed, alteration of the redox status in favor of a pro-oxidant microenvironment is likely caused by decreasing antioxidant enzyme activity, resulting in increased ROS production and subsequent deleterious immune system activation, as evidenced by macrophage over-activation during inflammatory processes.

Interestingly, increasing age is also associated with increased ROS, thromboxane A2, and prostacyclin production from cycloxygenase enzymes. The aging process is also associated with the upregulation of numerous inflammatory genes and proteins, including IL-1b, IL-6, TNF-a, iNOS, Cox-2 and various adhesion molecules (ICAM-1, VCAM-1, P-selectin, and E-selectin). Indeed, NF-kB, considered a master regulator of the inflammatory process, is upregulated in a pro-oxidative environment and has been shown to be involved in a wide range of systemic inflammatory disorders such as Alzheimer's disease, cancer, multiple sclerosis, diabetes, and cardiovascular disease.

Metabolic Dysregulation

The primary organelle responsible for ROS production in the cell is the mitochondrion, a membrane-bound organelle found in most eukaryotic cells that is responsible for the generation of ATP and orchestrating other various cellular process including cell differentiation, cell death, and regulation of the cell cycle. Although ATP generation is of critical importance in fueling numerous cellular processes, production of ROS as a natural byproduct of oxidative phosphorylation represents both a benefit and a liability. Although circumscribed levels of ROS may serve as effective signaling molecules for the induction of protective cellular stress responses, excessive electron leakage from complexes I and III of the electron transport chain (ETC) and the subsequent formation of superoxide radicals and hydrogen peroxide often lead to oxidative damage of lipids, proteins and DNA.

Mitochondria are unique in that they possess with their own circular genome (mtDNA) that lie in close proximity to complexes I and III of the ETC, subjecting mtDNA to ROS-mediated damage. Although mtDNA is associated with protein-DNA complexes in the mitochondrial matrix called nucleoids (similar to histones in nuclear DNA) that offer some protection against oxidative damage, these nucleoids are not as effective as histones, thus increasing the susceptibility of the mitochondrial genome to oxidative damage resulting in deletions, strand breaks, and point mutations. Subsequent blocking of DNA transcription and replication may impair several metabolic functions that occur within the mitochondria such as ATP generation, amino acid metabolism, and fatty acid oxidation.

Other deleterious effects of oxidative mitochondrial damage outside of metabolic perturbations include inappropriate activation of apoptosis via mitochondrial outer membrane permeabilization and subsequent release of cytochrome c into the cytosol and the induction of the mitochondrial permeability transition pore (leading to inner membrane permeability during pathological conditions such as stroke or traumatic brain injury). Unsurprisingly, numerous disorders are characterized by defects in cell metabolism and oxidative phosphorylation and can be detected early in the course of the disease, including diabetes, hypertension, Parkinson's disease, glaucoma, and age-related macular degeneration.

SUMMARY OF THE INVENTION

From the above observations and notations, it is evident that a common etiological undertone comprising oxidative stress, inflammation, and metabolic dysregulation characterize numerous conditions or diseases that are both age and non-age related. Because various treatment options available for such conditions typically focus on a single pathway, protein, or other drug target that plays a pathophysioloigcal role in disease progression but not disease etiology, novel methods and formulations that collectively mitigate systemic oxidative stress, enhance mitochondrial biogenesis and functionality, and decrease or inhibit factors that contribute to a chronic inflammatory state are desperately needed.

In a preferred embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), metformin, N-acetyl-L-cysteine (NAC), Coenzyme Q10 (CoQ10), melatonin, and magnesium.

In another embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), curcumin, N-acetyl-L-cysteine (NAC), and Coenzyme Q10 (CoQ10), melatonin, and magnesium.

In yet another embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), epigallocatechin-3-gallate (EGCG), N-acetyl-L-cysteine (NAC), Coenzyme Q10 (CoQ10), melatonin, and magnesium.

In another embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), resveratrol, N-acetyl-L-cysteine (NAC), Coenzyme Q10 (CoQ10), melatonin, and magnesium.

In yet another embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), pyrroloquinoline quinone (PQQ), N-acetyl-L-cysteine (NAC), Coenzyme Q10 (CoQ10), melatonin, and magnesium.

In another embodiment, the present invention comprises a formulation for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), berberine, N-acetyl-L-cysteine (NAC), Coenzyme Q10 (CoQ10), melatonin, and magnesium.

In yet another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), metformin, N-acetyl-L-cysteine (NAC), Coenzyme Q10 (CoQ10), melatonin, and magnesium.

In another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), curcumin, N-acetyl-L-cysteine (NAC), Coenzyme Q10 (CoQ10), melatonin, and magnesium.

In yet another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), epigallocatechin-3-gallate (EGCG), N-acetyl-L-cysteine (NAC), Coenzyme Q10 (CoQ10), melatonin, and magnesium.

In another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), resveratrol, N-acetyl-L-cysteine (NAC), Coenzyme Q10 (CoQ10), melatonin, and magnesium.

In yet another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), pyrroloquinoline quinone (PQQ), N-acetyl-L-cysteine (NAC), Coenzyme Q10 (CoQ10), melatonin, and magnesium.

In another embodiment, the present invention comprises a method for the treatment of for the treatment of diseases or conditions associated with oxidative stress, inflammation, and metabolic dysregulation, comprising therapeutically effective amounts of a topical or orally administered beta-adrenergic receptor blocker, vitamins A, C, and E, zinc, selenium, lutein, copper, eicosapentaenoic acid (EPA), docosahexaenoic acid (DHA), acetylsalicylic acid (ASA), berberine, N-acetyl-L-cysteine (NAC), Coenzyme Q10 (CoQ10), melatonin, and magnesium.

From the aforementioned summary and disclosed embodiments, an apparent object of the present invention is the development of novel methods and formulations that are effective in mitigating the deleterious effects of oxidative stress and chronic inflammation while positively influencing the rate and efficiency of mitochondrial biogenesis and energy production. The present invention is capable of being practiced in variation and is not limited to details set forth in the following description of the invention.

DETAILED DESCRIPTION OF THE INVENTION

The following written description of the invention and the manner and process of making and using it, in full, clear, concise, and exact terms, is provided to enable any person skilled in the art to make and use the same and sets forth the best mode of carrying out the invention.

The preferred embodiment of the present invention consists of a novel composition comprising the administration of a topical beta-adrenergic receptor blocker, vitamins A, C, and E, zinc, selenium, lutein, copper, eicosapentaenoic acid (EPA), docosahexaenoic acid (DHA), acetylsalicylic acid (ASA), metformin, N-acetyl-L-cysteine (NAC), Coenzyme Q10 (CoQ10), melatonin, and magnesium.

TABLE

| Composition | Daily Dosage |
| --- | --- |
| Vitamin A | 6,000 IU |
| Vitamin C | 1,200 mg |
| Vitamin E | 360 IU |
| Zinc | 240 mg |
| Selenium | 330 mcg |
| Copper (cupric oxide) | 12 mg |
| Lutein | 12 mg |
| Eicosapentaenoic acid (EPA) | 1,860 mg |
| Docosahexaenoic acid (DHA) | 1,500 mg |
| Acetylsalicylic acid (ASA) | 650 mg |
| Timolol 0.5% | Two drops per eye |
| Metformin | 500 mg |
| N-acetyl-L-cysteine (NAC) | 1200 mg |
| CoQ10 | 200 mg |
| Melatonin | 5 mg |
| Magnesium | 500 mg |

Oral administration, in the form of tablets, coated tablets, time-released tablets, or capsules, is preferred for the administration of vitamins A, C, and E, zinc, selenium, copper, lutein, EPA, DHA, ASA, metformin, NAC, CoQ10, melatonin, and magnesium. For the sake of duplicative avoidance, throughout the remainder of the written description the term "capsule" will be used and shall include the use of tablets, coated tablets, time-released tablets, or any variations thereof.

Particularly, the daily dosage comprising the preferred embodiment may be administered through oral ingestion of at least one capsule containing 3000 IU of vitamin A twice per day for a minimum of thirty consecutive days, at least one capsule containing 600 mg of vitamin C twice per day for a minimum of thirty consecutive days, at least one capsule containing 180 IU of vitamin E twice per day for a minimum of thirty consecutive days, at least one capsule containing 120 mg of zinc twice per day for a minimum of thirty consecutive days, at least one capsule containing 165 mcg of selenium twice per day for a minimum of thirty consecutive days, at least one capsule containing 6 mg of copper (cupric oxide) twice per day for a minimum of thirty consecutive days, at least one capsule containing 6 mg of lutein twice per day for a minimum of thirty consecutive days, at least one capsule containing 465 mg of EPA four times per day for a minimum of thirty consecutive days, at least one capsule containing 375 mg of DHA four time per day for a minimum of thirty consecutive days, at least one capsule containing 325 mg of ASA twice per day for a minimum of thirty consecutive days, at least one capsule containing 500 mg of metformin once per day for a minimum of thirty consecutive days, at least one capsule containing 600 mg of NAC twice per day for a minimum of thirty consecutive days, at least one capsule containing 200 mg of CoQ10 once per day for a minimum of thirty consecutive days, at least one capsule containing 5 mg of melatonin once per day for a minimum of thirty consecutive days, and at least one capsule containing 250 mg of magnesium twice per day for a minimum of thirty consecutive days Topical ocular administration, in the form of an aqueous maleate ophthalmic solution, is preferred for the administration of Timolol 0.5%. The daily application comprising the preferred embodiment may be administered through at least two drops of Timolol 0.5% per eye for a minimum of thirty consecutive days.

Alternative methods of administration outside of oral ingestion and topical administration are also contemplated herein, including, but not limited to, subcutaneous, intramuscular, intraperitoneal, sublingual, intravenous, percutaneous, or like methods.

The composition of the present invention is formulated to provide the described essential ingredients in amounts to preferably not fall below that of the preferred embodiment. Such preferred amounts of the essential ingredients have been shown to act synergistically to effect a near complete regression of two pathological conditions associated with oxidative stress, inflammation, and metabolic dysregulation: (1) ocular choroidal neovascularization secondary to exudative AMD; and (2) microvascular endothelial cell proliferation secondary to an abnormal nodular growth localized to the thyroid gland, as illustrated in the following two examples.

Case 1

The subject was presented with exudative age-related macular degeneration and exhibited severe central vision loss in his right eye. Vision loss occurred rapidly over a period of forty-five days from the time of initial visual changes noted by the subject. Vision loss continued for an additional thirty consecutive days until the preferred embodiment of the present invention was administered. Within thirty days, central visual loss as a result of ocular choroidal neovascularization secondary to age-related macular degeneration showed complete regression with return of vision in the subject's right eye that exceeded visual acuity of the originally unaffected left eye. It should be noted that the dry form (drusen-associated) of age-related macular degeneration seemed not to be affected by the administration of the preferred embodiment of the present invention.

Case 2

The subject was presented with a slow but progressive increase in an apparent thyroid nodule localized to the right side of the thyroid gland. The subject had already been diagnosed with hypothyroidism and was currently taking levothyroxine sodium for the condition. Increasing doses of levothyroxine sodium did not seem to inhibit the growth of the nodule. The nodule reached an approximate size of 7.5 centimeters by 5 centimeters by 2 centimeters. After the subject was administered the preferred embodiment of the present invention, the nodule decreased in size to tactile (perceptible by touch) only presence. It is important to note that the subject was continually administered levothyroxine sodium both during and after the administration of the preferred embodiment of the present invention. Anecdotally, upon optometric examination subsequent to administration of the preferred embodiment of the present invention, the subject's visual acuity was normalized to 20/20 via Snellen chart measurements.

Each tablet and milliliter of aqueous solution comprising the preferred and additional embodiments of the present invention preferably contains the following essential ingredients in clinically therapeutic amounts as described and further specified below.

Vitamin A

Vitamin A, a generic term for a larger number of compounds, is often used to describe vitamin A precursors falling primarily into two classes, preformed vitamin A and provitamin A carotenoids. Preformed vitamin A, the form of vitamin A that comprises the preferred dosage of the present invention, is often associated with the compounds retinol (an alcohol) and retinal (an aldehyde).

Retinal may be converted by the body into retinoic acid, a member of the retinoid class which has been shown to influence the rate of gene transcription and thus the regulation of protein synthesis and numerous other physiological processes. Initially, two isoforms of retinoic acid (RA), all-trans-RA and 9-cis-RA, are transported from the cytoplasm into the nucleus of the cell through binding of cytoplasmic retinoic acid-binding proteins (CRABP). Within the nucleus, all-trans-RA binds to retinoic acid receptors (RAR) and 9-cis-RA binds to retinoid X receptors (RXR). After undergoing heterodimerization, the RAR/RXR complex binds to a chromosomal regulatory portion within the nucleus termed retinoic acid response elements (RARE). Through the initiation of a biochemical cascade that results in RARE binding alongside heterodimerization with receptors such as thyroid hormone receptor (THR), retinoic acid may stimulate or inhibit transcription of specific genes associated with oxidative stress, inflammation, and mitochondrial respiration. For example, methionine sulfoxide reductases (MSRs) are a family of antioxidant enzymes that play a critical role in protection against oxidative stress (by converting protein-bound methionine sulfoxide back to methionine) and its overexpression, particularly MSRA, leads to increased resistance to oxidative stress and hypoxia in yeast and human cell lines. The MSRA gene is highly expressed in the brain and retinal pigment epithelial cells and contains two promoters that code for a mitochondrial-localized and a cytosol-localized isoform, respectively. Both promoters have been shown to respond vigorously to all-trans retinoic acid, the acid form of vitamin A.

Retinol, a metabolite of vitamin A, has been shown to be essential to the metabolic efficiency of mitochondria by physically binding to PKCδ. Such binding creates a PKCδ/retinol complex that signals the pyruvate dehydrogenase complex, enhancing the flux of pyruvate into the Krebs cycle. Retinoic acid has also been shown to inhibit inflammatory mediators such as NF-kB, IL-6, COX-2, and MCP-1 and upregulate anti-inflammatory mediators such as kallistatin and eNOS. Retinoic acid use has also been proven beneficial in numerous diseases states, including Alzheimer's disease (upregulation of the alpha-secretase ADAM10 and activation of AMPK), cancer (induction of thrombospondin-1 and inhibition of ICAM-1), autoimmune disorders (increases Foxp3+ regulatory T cells and inhibits development of Th17 cells), and cognitive disorders (enhances phosphatidylcholine biosynthesis and hippocampal neurogenesis).

Accordingly, the daily dosage of vitamin A comprising the preferred embodiment may be administered through oral ingestion of at least one capsule containing 3000 IU of preformed vitamin A twice per day for a minimum of thirty consecutive days.

Vitamin C

Vitamin C exists in two forms, the L- and D-enantiomers of ascorbate. L-ascorbate, or ascorbic acid, is the only form of vitamin C of physiological significance and is well known for its antioxidant activity. Both forms are mirror images of the same molecular structure.

When undergoing oxidative stress, affected cells and tissues may accelerate the formation of reactive oxygen species or free radicals in response to diseases or conditions including hypertension, diabetes, chronic inflammation, and cancer. Ascorbic acid acts as an antioxidant by facilitating energetically favorable reduction-oxidation (redox) reactions. Free radicals such as hydroxyl are highly reactive and potentially damaging at the cellular level due to the interaction of an unpaired electron with proteins, lipids, or nucleic acids. During a reduction-oxidation reaction involving ascorbate, free radical oxidation of ascorbic acid to dehydro-ascorbate is followed by the reduction of the free radical to water. The resulting stability and non-reactiveness of oxidized ascorbic acid avoids cellular damage while mitigating the effects of highly reactive oxygen species through reduction.

A number of studies have shown that higher intakes of vitamin C are associated with a decrease in the incidence of various cancers, including cancers of the stomach, colon, lungs and throat (Carr, A. C., et al. 1999. Toward a new recommended dietary allowance for vitamin C based on antioxidant and health effects in humans. Am J Clin Nutr. 69(6): 1086-1107). Particularly, in carcinogenesis-induced mouse models through intraperitoneal injection of sarcoma S-180 cells, subsequent administration of high dose vitamin C increased the survival rate by 20% as compared to control models (Yeom C. H., et al. 2009. High dose concentration administration of ascorbic acid inhibits tumor growth in BALB/C mice implanted with sarcoma 180 cancer cells via the restriction of angiogenesis. J Transl Med. 11: 70). Researchers also found that in mice with the highest survival rates, vitamin C inhibited the expression of three angiogenesis-related genes responsible for the production bFGF, VEGF and MMP2 by 0.3 times, 7 times and 4 times, respectively, lending credence to the belief that angiogenesis-mediated carcinogenesis may be susceptible to high dose vitamin C administration.

L-dehyrdoascorbic acid, the oxidized form of vitamin C, has also been shown to localize to the mitochondria via GLUT10 transport, offering further protection from oxidative stress in cells such as smooth muscle cells and insulin-stimulated adipocytes. Other diseases states and conditions in which ascorbic acid has been shown to be efficacious include Alzheimer's disease (inhibition of Cox-2-mediated prostaglandin E2 production), DNA repair (inhibition of AP-1 and upregulation of MLH1), and rheumatoid arthritis (inhibition of HIF-1 alpha).

Accordingly, the daily dosage of vitamin C comprising the preferred embodiment may be administered through oral ingestion of at least one capsule containing 600 mg of vitamin C twice per day for a minimum of thirty consecutive days.

Vitamin E

Vitamin E, a well established antioxidant, is comprised of eight derivative antioxidants falling primarily into two classes: tocotrienols (alpha, beta, gamma, and delta) and tocopherols (alpha, beta, gamma, and delta). Alpha-tocopherol, largely concentrated in the blood and tissues through the action of alpha-tocopherol transfer protein, is the only vitamin E derivative actively maintained by the human body and thus has the greatest physiological significance for pathological conditions.

Alpha-tocopherol's antioxidant capabilities appear to reside in its ability to induce phase II antioxidant enzymes via upregulation of Nrf2 and to neutralize free radicals generated as a result of normal metabolic processes or exposure to deleterious environmental conditions such as sunlight, pollutants, or cigarette smoke. It is thought that alpha-tocopherol, a fat-soluble vitamin, protects cell membranes from oxidation by interacting with and removing lipid free radical intermediates produced by the lipid peroxidation chain reaction, preventing the continuation of the oxidation reaction. Although alpha-tocopherol's antioxidant capacity is lost upon free radical neutralization, concurrent administration of other antioxidants such as vitamin C may serve to reestablish alpha-tocopherol's antioxidant capabilities.

Certain cancers are thought to be the result of both oxidative damage to DNA caused by free radicals and uncontrolled cellular proliferation or resistance to programmed cell death (apoptosis). Studies utilizing cell cultures have indicated that alpha-tocopheryl succinate, a vitamin E ester, may inhibit cellular proliferation or induce cancer cell apoptosis (Neuzil, J., et al. 2001. Induction of cancer cell apoptosis by alpha-tocopheryl succinate: molecular pathways and structural requirements. FASEB J. 15(2):403-415). Because alpha-tocopheryl succinate is devoid of any antioxidant activity, it has been argued that vitamin E esters and derivatives are capable of inhibiting uncontrolled cellular growth and proliferation via a multifactor process (Brigelius-Flohe, R., et al. 2002. The European perspective on vitamin E: current knowledge and future research. Am J Clin Nutr. 76(4):703-716). Additionally, studies have also shown that vitamin E may inhibit tumor angiogenesis and carcinogenesis via selective inhibition of transforming growth factor-alpha (Shklar, G., et al. 1996. Vitamin E inhibits experimental carcinogenesis and tumour angiogenesis. Eur J Cancer B Oral Oncol. 32B(2):114-9).

The antioxidant properties of alpha-tocopheryl have also been shown to reduce mitochondrial superoxide and hydrogen peroxide generation as well as the inflammatory mediators IL-4, IL-5, IL-13, and transendothelial migration of neutrophils in response to airway inflammation. Due to its ability to activate the nuclear receptor PPARgamma via upregulation of adiponectin, alpha-tocopheryl has also been shown to be effective in animal models of Alzheimer's disease (repression of beta-secretase gene promoter activity, decreased Abeta 1-40 concentration in the brain, and induction of brain mitochondrial biogenesis).

Accordingly, the daily dosage of vitamin E comprising the preferred embodiment may be administered through oral ingestion of at least one capsule containing 180 IU of vitamin E twice per day for a minimum of thirty consecutive days.

Zinc

Zinc, an essential trace element for all life forms, is a metallic chemical agent that is found in nearly 100 specific enzymes, serving as a catalyst for numerous cellular metabolic processes due to its affinity to serve as an effective electron pair acceptor. Zinc is also recognized as the second most abundant transition metal and is often stored and transferred in metallothioneins. Additionally, due to its flexible coordination geometry, zinc also potentiates a rapid shift in protein conformation allowing for further mediation of biological reactions, such as protein digestion and carbon dioxide production via carboxypeptidase and carbonic anhydrase, respectively.

Due to zinc's ability to stabilize the structure of proteins and cell membranes though the development of antioxidant enzymes such as superoxide dismutase (CuZnSOD), susceptibility of biological membranes to oxidative damage may be attenuated (Ugarte, M., et al. 2001. Zinc in the retina. Prog Neurobiol. 64(3): 219-49). It is also known that zinc deficiency may interfere with the metabolism of vitamin A metabolites (e.g. retinoic acid) through decreased synthesis of retinol-binding proteins and retinol-associated release enzymes (required by the liver to release retinol). Indeed, studies have shown that concomitant administration of zinc and antioxidants proved more efficacious in treating pathological conditions characterized by angiogenesis and free radical generation such as exudative AMD than monotherapy (Wood, J., et al. 2003. Zinc and Energy Requirements in Induction of Oxidative Stress to Retinal Pigmented Epithelial Cells. Neurochemical Research. 28(10).

Zinc has also been shown to increase intracellular ATP levels via activation of AMPK through leptin upregulation. Increased levels of ATP along with the administration of extracellular zinc was shown to increase chloride secretion across cystic fibrosis airway epithelia by triggering calcium entry. Zinc has also been shown to be necessary for the anti-tumor activity of the anti-angiogenic mediator endostatin (zinc (II) binds to the N-terminal 25-mer peptide fragment of human endostatin), suppression of autoimmune diseases (inhibits the development of Th17 cells via attenuating STAT3 activation), and mitigating the effects of inflammatory mediators in mouse models of allergic inflammation (zinc supplementation decreased bronchoalveolar lavage fluid eosinophils and lymphocytes).

Accordingly, the daily dosage of zinc comprising the preferred embodiment may be administered through oral ingestion of at least one capsule containing 120 mg of zinc twice per day for a minimum of thirty consecutive days.

Selenium

Selenium, an essential micronutrient that is toxic at large doses, is required by animals and humans for the facilitation of various selenium-dependent enzymes or selenoproteins.

Functional selenoproteins are formed through the incorporation of selenocystine into specific amino acid sequence locations. Several selenoproteins express distinct antioxidant activity utilizing a ubiquitous oxidation-reduction reaction. For example, a five-member class of selenoproteins known as glutathione peroxidases (GPX) function primarily as antioxidant enzymes by reducing damaging reactive oxygen species (ROS), such as lipid hydroperoxides and hydrogen peroxide, to harmless byproducts such as alcohol and water. Specifically, in a reaction catalyzed by the selenoenzyme glutathione peroxidase, two molecules of glutathione are oxidized while one molecule of hydrogen peroxide is reduced to two molecules of water. Additional studies also indicate that GPX appears to enhance the activity of vitamin E by limiting lipid oxidation and mitigating oxidative stress-induced damage as a result of vitamin E deficiency (Sword, J. T., et al. 1991. Endotoxin and lipid peroxidation in vitro in selenium- and vitamin E-deficient and -adequate rat tissues. J Nutr. 121(2): 258-264).

In addition to its antioxidant capabilities, members of other selenoprotein classes appear to play essential roles in various metabolic processes, including antioxidant regeneration (thioredoxin reductase and glutathione peroxidase), hormonal activation and inactivation (selenium-dependent iodothyronine deiodinase enzymes), protein transportation (selenoprotein P), cancer prevention (15 kDA selenoprotein), and misfolded protein translocation and inflammation response (selenoprotein S).

Well over sixty published studies involving various animal models of induced carcinogenesis indicate that methylated selenium, a metabolite produced as a result of excess selenium intake, significantly reduces tumor incidence (Whanger, P. D., et al. 2004. Selenium and its relationship to cancer: an update. Br J Nutr. 91(1):11-28; Ip, C. 1998. Lessons from basic research in selenium and cancer prevention. J Nutr. 128(11):1845-1854). Several models have been proposed to explicate the anti-carcinogenic effects of selenium, including activity maximization of antioxidant selenoenzymes, regulation of apoptosis, metabolite inhibition of tumor cell growth, regulation of DNA repair, and inhibition of angiogenesis (Combs, G. F. et al. 1998. Chemopreventive agents: selenium. Pharmacol Ther. 79(3):179-192). Several studies indicate that methlyselenic acid (MseA) and methlyselenocyanate inhibited matrix metalloproteinase-2 activity in human umbilical vein endothelial cells in a concentration-dependent manner (Lu, J., et al. 2001. Antiangiogenic activity of selenium in cancer chemoprevention: metabolite-specific effects. Nutr Cancer. 40(1):64-73; Jiang, C., et al. 2000. Monomethyl selenium-specific inhibition of MMP-2 and VEGF expression: implications for angiogenic switch regulation. Mol. Carcinog. 29:236-250). Additionally, cellular and secreted protein levels of VEGF in human prostate and breast cancer cells were decreased as a result of MseA administration. High dose selenium intake also appeared to reduce VEGF release, intratumoral microvessel density, and melanoma cell metastasis in rat mammary carcinomas (Jiang, C., et al. 1999. Selenium-induced inhibition of angiogenesis in mammary cancer at chemopreventive levels of intake. Molec Carcinogenesis. 26: 213-225; Yan, H., et al. 1999. Dietary supplementation of selenomethionine reduces metastasis of melanoma cells in mice. Anticancer Res. 19(2A):1337-42).

Selenium supplementation has also been found to inhibit human colon cancer cells by upregulating AMPK, leading to a decrease in the activities of mTOR and COX-2, and activation of ATM-dependent DNA damage response via the mismatch repair protein hMLH1. Higher dose selenium supplementation has also been shown to attenuate neutrophil infiltration and myeloperoxidase activity and increase the levels of nuclear respiratory factor-1 and mitochondrial transcription factor-A in a rat model of colitis and reduce the levels TNF-alpha, IL-8, and NF-kB, leading to an inhibition of HIV-1 LTR promoter activity.

Accordingly, the daily dosage of selenium comprising the preferred embodiment may be administered through oral ingestion of at least one capsule containing 165 mcg of selenium twice per day for a minimum of thirty consecutive days.

Copper (Cupric Oxide)

Copper (Cu), another essential trace element in mammals, has the ability to shift between the cupric and cuprous forms, though the majority of copper in the body exists in the cupric form. As with other well known vitamins and minerals, copper exerts potent antioxidant activity and thus facilitates oxidation-reduction reactions by mitigating free radical production through donation and acceptance of electron pairs.

Although a number of enzymes (e.g., cuproenzymes) are critically dependent on the availability of copper to promote various physiological processes, copper's role in facilitating the formation of antioxidant-promoting enzymes has shown the most promise in addressing pathological conditions associated with free radical formation. For example, superoxide dismutase (SOD) functions as an antioxidant through the catalysis of reactive oxygen species (ROS) or superoxide radicals to hydrogen peroxide. Hydrogen peroxide may be subsequently reduced to water by other antioxidants (Johnson, M. A., et al. 1992. Is copper an antioxidant nutrient? Crit Rev Food Sci Nutr. 32(1):1-31). Two forms of copper-incorporated SOD include copper/zinc SOD (found within a variety of body cells such as red blood cells) and copper-containing extracellular SOD (found within the lungs and blood plasma) (Turnlund, J. R. 2006. Copper. In: Shils M E et al. Modern Nutrition in Health and Disease, 10th ed. Philadelphia: Lippincott Williams & Wilkins).

Another copper-containing enzyme that may function as an antioxidant is ceruloplasmin. Because free iron and copper ions are known catalysts of free radical damage, ceruloplasmin's biding of copper ions may prevent such ions from catalyzing oxidative damage. Additionally, iron loading onto its transport protein (transferrin) is facilitated by the ferroxidase activity of ceruloplasmin, possibly preventing free ferrous ions ($Fe^{2+}$) from participating in free radical generation (Johnson, M. A. et al. 1992. Is copper an antioxidant nutrient? Crit Rev Food Sci Nutr. 32(1):1-31).

The incorporation of copper into transcription factors may also affect protein synthesis by inhibiting or enhancing specific gene transcription. Such copper-dependent transcription factors are known to regulate genes that encode for catalase (an antioxidant), copper/zinc superoxide dismutase (Cu/Zn SOD), and copper storage proteins (Uauy, R., et al. 1998. Essentiality of copper in humans. Am J Clin Nutr. 67(5 Suppl):952S-959S). Copper's antioxidant-inducing properties have also been demonstrated in prion diseases such Creutzfeldt-Jakob disease (a fatal neurodegenerative disease), in which the normal function of the cellular prion protein appears to be that of an antioxidant (copper binding to the cellular prion protein induces a superoxide dismutase-like activity).

Accordingly, the daily dosage of copper comprising the preferred embodiment may be administered through oral ingestion of at least one capsule containing 6 mg of copper (cupric oxide) twice per day for a minimum of thirty consecutive days.

Lutein

Lutein is one of more than 600 naturally occurring pigments known as carotenoids. Primarily synthesized by algae, plants, and photosynthetic bacteria, lutein exists in the form of fatty acid esters, with hydroxyl groups bound to at least one ester. The subsequent hydrolysis of the esters under basic conditions (saponification) yields lutein in an approximately 1:2 molar ratio. The most common dietary carotenoids include alpha-carotene, beta-carotene, beta-cryptoxanthin, lycopene, lutein, and zeaxanthin. Lutein, zeaxanthin, and beta-cryptoxanthin are further subcategorized into a class of carotenoids known as xanthophylls, with lutein and zeaxanthin possessing the ability to absorb blue light and thus appearing yellow at low concentrations and orange-red at higher concentrations.

Lutein and other members of the carotenoid class are known to promote antioxidative functions in plants through either deactivation of singlet oxygen during photosynthesis or the inhibition of lipid peroxidation under specified conditions. In vivo animal models and in vitro studies have also demonstrated that lutein may accumulate in the skin of mice via dietary supplementation, leading to a decrease in ROS generation after ultraviolet radiation exposure and inhibit MMP-1 expression while stimulating TIMP-2 activity in melanoma cells, respectively.

Lutein and zeaxanthin are the only carotenoids found in the retina, with particularly high concentrations in the macula. Thus, protection against light-induced oxidative damage through the prevention of retinal exposure to blue light is thought to be the primary mechanism of action in which lutein may slow or prevent the onset of age-related macular degeneration (Krinsky, N. I., et al. 2003. Biologic mechanisms of the protective role of lutein and zeaxanthin in the eye. Annu Rev Nutr. 23:171-201). In addition to light-absorbing protective effects offered by carotenoids, studies have also shown that elevated intakes of lutein and zeaxanthin may be associated with a lower risk of age-related macular degeneration due to direct neutralization of oxidants in the retina (Mares-Perlman, J. A., et al. 2002. The body of evidence to support a protective role for lutein and zeaxanthin in delaying chronic disease. Overview. J Nutr. 132(3):518S-524S). Indeed, after ranking participants into five groups according to the amount of dietary intake of lutein and zeaxanthin, researchers in the Age-Related Eye Disease Study (AREDS) found that the group who had the highest intake of either carotenoid experienced a forty percent reduction in the risk of developing atrophic or neovascular AMD, leading to the notion that lutein and zeaxanthin may posses both anti-angiogenic and antioxidative capabilities (Berthold, P., et al. 2009. Effects of Antioxidants (AREDS Medication) on Ocular Blood Flow and Endothelial Function in an Endotoxin-induced Model of Oxidative Stress in Humans. Invest. Ophthalmol. Vis. Sci. 0:iovs.09-3888v1).

The role of lutein and other carotenoids in regulating cellular proliferation and angiogenesis during pathological states has been further elucidated through the recognition of carotenoid-induced up regulation of genes coding for a connexin protein (Bertram, J. S., et al. 1999. Carotenoids and gene regulation. Nutr Rev. 57(6):182-191). Connexins allow cells to communicate via small molecule exchanges through cellular pores or gap junctions. Communication facilitation though gap junctions promote the maintenance of cellular differentiation, an ability that is often lost in cancer cells (Stahl, W., et al. 1997. Biological activities of natural and synthetic carotenoids: induction of gap junctional communication and singlet oxygen quenching. Carcinogenesis. 18(1): 89-92). Another study also revealed that lutein administration inhibited mouse mammary tumor growth by increasing the expression of proapoptotic genes p53 and Bax, together with a decrease in the antiapoptotic gene Bcl-2. Moreover, lutein-fed mice in the study experienced a decrease in angiogenic activity in mammary tumors as compared to unsupplemented mice (Chew, B. P., et al. 2003. Dietary lutein inhibits mouse mammary tumor growth by regulating angiogenesis and apoptosis. Anticancer Res. 23(4):3333-9). Similar results have also been observed in human models of colon cancer in the presence of carotenoids such as lutein or zeaxanthin (Ka, C. H., et al. 2008. Antiproliferative effects of carotenoids extracted from *Chlorella ellipsoidea* and *Chlorella vulgaris* on human colon cancer cells. J Agric Food Chem. 56(22): 10521-6).

Accordingly, the daily dosage of lutein comprising the preferred embodiment may be administered through oral ingestion of at least one capsule containing 6 mg of lutein twice per day for a minimum of thirty consecutive days.

Eicosapentaenoic Acid (EPA) and Docosahexaenoic Acid (DHA)

Eicosapentaenoic acid (EPA, C20:5) and docosahexaenoic acid (DHA, C22:6) are omega-3 polyunsaturated fatty acids (PUFA) found primarily in fish oil. EPA has been shown to interact with metabolites of arachidonic acid (AA, C20:4) to form prostaglandin-3, thromboxane-3, leukotrine-5, and other members of the eicosanoid class. DHA, which is either present in the diet or derived from EPA via docosapentaenoic acid (DPA, C22:5) as an intermediate, is metabolized to form docosanoids and is known to be the most abundant PUFA in the brain and retina, comprising 40% and 60% of all constituent PUFAs, respectively. EPA and DHA can be provided in the form of omega-3-acid ethyl esters.

Although it is well known that arachidonic acid may be converted via the cycloxygenase (COX) or lipoxygenase (LOX) pathway into eicosanoid mediators such as leukotrienes, prostaglandins, and lipoxins (Nelson, G. J., et al. 1997. The effect of dietary arachidonic acid on platelet function, platelet fatty acid composition, and blood coagulation in humans. Lipids. 32(4):421-5), only recently has it been shown that the acetylation of COX-2 by acetylsalicylic acid (ASA) in the presence of EPA or DHA yields potent anti-inflammatory mediators termed resolvins and protectins (Serhan, C. N., et al. 2004. Resolvins, docosatrienes, and neuroprotectins, novel omega-3-derived mediators, and their aspirin-triggered endogenous epimers: an overview of their protective roles in catabasis. Prostaglandins & Other Lipid Mediators. 73(3-4)155-172). Though such key mediators of omega-3 PUFA metabolism has only been recently elucidated, the physiological benefits of omega-3 PUFA supplementation has long been noted for diseases and conditions mediated by inflammation or oxidative stress, including cancer (Begin, et al. 1986. Differential Killing of Human Carcinoma Cells Supplemented with N-3 and N-6 Polyunsaturated Fatty Acids. J Natl Cancer Inst. 77(5):1053-1062), coronary heart disease (Shekelle, R. B., et al. 1985. Fish consumption and mortality from coronary heart disease. N Engl J Med. 313: 820), and autoimmune disease (Simopoulos, P. 2002. Omega-3 Fatty Acids in Inflammation and Autoimmune Diseases. Journal of the American College of Nutrition. 21(6): 495-505). Additionally, through upregulation of AMPK, omega-3 PUFA supplementation has also been shown to facilitate and enhance mitochondrial biogenesis and beta-oxidation of fatty acids.

Such pleiotropic effects of EPA and DHA have proven efficacious in numerous disease states, including Alzheimer's disease (upregulation of neuroprotectin D1, reduction of amyloid beta production, down regulation of beta-secretase-1, and upregulation of alpha-secretase ADAM10), atherosclerosis (decrease in macrophage-induced tissue inflammation and downregulation of NF-kB, AP-1, and VCAM-1), and multiple sclerosis (inhibition of MMP-9, prevention of dendritic cell maturation, and inhibition of antigen-specific Th1/Th17 differentiation).

Accordingly, the daily dosage of EPA comprising the preferred embodiment may be administered through oral ingestion of at least one capsule containing 465 mg of EPA four times per day for a minimum of thirty consecutive days.

Accordingly, the daily dosage of DHA comprising the preferred embodiment may be administered through oral ingestion of at least one capsule containing 375 mg of DHA four times per day for a minimum of thirty consecutive days.

Acetylsalicylic Acid (ASA)

Acetylsalicylic acid (ASA), a well known salicylate drug and the primary metabolite of aspirin, possesses anti-pyretic, anti-inflammatory, antioxidant, and analgesic properties and is included within a class of compounds known as non-steroidal anti-inflammatory drugs (NSAIDs). Although ASA's mechanism of action is similar to that of other NSAIDs (i.e. inhibiting the enzyme cycloxygenase), ASA appears to differ from other NSAIDs in that inhibition of cycloxygenase by ASA occurs via irreversible acetylation of a serine residue located in the active site of the cycloxygenase enzyme, resulting in decreased production of prostaglandins and thromboxanes, accounting for ASA's anti-platelet and anti-inflammatory effects.

Although ASA irreversibly inhibits the COX-1 isoenzyme of cycloxygenase, ASA only modifies the enzymatic activity of COX-2, leading to the production of potent anti-inflammatory mediators known as lipoxins. Interestingly, recent research has shown that production of two novel and powerful anti-inflammatory metabolites derived from omega-3 fatty acids, resolvins and protectins, are enhanced via the actions of an ASA-acetylated COX-2 isoenzyme.

In addition to its well noted anti-inflammatory effects, ASA administration has also been shown to reduce the incidence of various cancers (NF-kB down regulation, COX-2 inhibition, MMP-2 reduction, increased E-cadherin production, and reduction in beta-catenin/TCF complex), enhance anti-oxidative processes (inhibition of TNF-alpha production and lipid peroxidation, increase in heme oxygenase-1, catalase, EC-SOD, and Nrf-2 and reduction of superoxide anion), increase mitochondrial biogenesis and respiration (increase in HO-1, Nrf-2, and NRF-1 and activation of AMPK), and promote DNA repair (increase in ATM, XRCC3, and GADD45-alpha).

Accordingly, the daily dosage of ASA comprising the preferred embodiment may be administered through oral ingestion of at least one capsule containing 325 mg of ASA twice per day for a minimum of thirty consecutive days.

Timolol 0.5%

Non-selective beta-adrenergic receptor blockers are available via oral or topical administration and exert their physiological effects through binding and antagonizing beta-adrenergic receptors. Adrenergic receptors are a subset of a larger class of receptors known as G-protein coupled receptors (GPCRs). Ligands for adrenergic receptors primarily include two well-known members of the catecholamine class, epinephrine and norepinephrine. Agonist binding to adrenergic receptors will generally cause a sympathetic response, including heart muscle contraction, smooth muscle relaxation, and lipolysis enhancement.

The adrenergic receptor class includes both alpha and beta type receptors, with an increasing focus on beta receptors as primary targets for pharmacological intervention. There are three known types of beta receptors, designated $\beta 1$, $\beta 2$, and $\beta 3$. $\beta 1$-adrenergic receptors are located largely in the heart and kidneys while $\beta 3$-adrenergic receptors are generally located in fat cells. $\beta 2$-adrenergic receptors, by far the most ubiquitous of the beta receptors, are found in the eye, lungs, uterus, gastrointestinal tract, vascular smooth muscle, and skeletal muscle.

Topical non-selective beta-adrenergic receptor blockers have proven efficacious in diseases of the eye such as glaucoma through antagonism of $\beta 2$-adrenergic receptors located in the ciliary body, resulting in a reduction of aqueous humor production. However, such topical beta blockers are thought to be ineffective in addressing pathological conditions of posterior eye portions such as exudative AMD or other systemic diseases characterized by abnormal angiogenesis due to the perceived failure of the topical beta blocker to achieve adequate systemic delivery. However, several studies have noted systemic side effects from absorption into the bloodstream from the topical application of Timolol paralleling those seen with systemic administration of non-selective beta blockers (Nieminen, T., et al. 2007. Ophthalmic timolol: plasma concentration and systemic cardiopulmonary effects. Scand J Clin Lab Invest. 67(2):237-45; Uusitalo, H., et al. Efficacy and systemic side-effects of topical 0.5% timolol aqueous solution and 0.1% timolol hydrogel. Acta Ophthalmologica Scandinavica. 83(6):723-728).

Thus, in addition to the cumulative effects derived from the co-administration of selected antioxidant vitamins, phytochemicals, and minerals, it is thought that the systemic effects of topical Timolol application acts synergistically with EPA:DHA:ASA metabolite formation (i.e. resolvins and protectins) to significantly enhance anti-angiogenic and anti-oxidative processes several fold. Two mechanisms of action are proposed to explain the observation of such enhanced antiangiogenic processes and antioxidant formation.

As noted previously, $\beta 2$-adrenergic receptors may be found in many tissues, including vascular smooth muscle cells, where receptor activation results in smooth muscle relaxation. Receptor ChemR23, a receptor to which metabolites of EPA and DHA bind, is also profusely populated in the smooth muscle vasculature and belongs to the G-protein coupled receptor family (GPCR) (Cash, J., et al. 2008. Synthetic chemerin-derived peptides suppress inflammation through ChemR23. J Exp Med. 205(4): 767-775). It has also been shown that EPA and DHA metabolites may bind to other members of the GPCR family to effectively regulate the production and release of mediators involved in inflammation (Arita, M., et al. 2007. Resolvin E1 selectively interacts with leukotriene B4 receptor BLT1 and ChemR23 to regulate inflammation. J Immunol. 178(6):3912-7). Thus, a dual agonist/antagonist mechanism of action is inferred whereby a natural ligand for ChemR23 (Resolvin E1) may bind to a $\beta 2$-adrenergic receptor and a non-selective $\beta 2$-adrenergic receptor blocker (Timolol) may bind to receptor ChemR23.

Studies have shown that cancer cells may release angiogenic mediators such as IL-6, IL-8, and VEGF under conditions of stress, likely mediated through cell-surface receptor binding of the known stress hormones epinephrine and norepinephrine. (Yang, E. V., et al. 2009. Norepinephrine upregulates VEGF, IL-8, and IL-6 expression in human melanoma tumor cell lines: implications for stress-related enhancement of tumor progression. Brain, Behavior, and Immunity. 23:267-275). Because a β2-adrenergic receptor is coupled to adenylyl cyclase, natural ligand (e.g. epinephrine) binding to a β2-adrenergic receptor would result in an elevation in cAMP levels, possibly resulting in angiogenic mediator release by stress-induced cancer cells. However, because it has also been shown that Resolvin E1 binding to the leukotriene B4 receptor BLT 1 (a G-protein coupled receptor involved in the chemotaxis of inflammatory mediators) selectively inhibited BLT 1 adenylyl cyclase activity, Resolvin E1 binding to β2-adrenergic receptors may also induce a similarly antagonistic effect and thus reduce IL-6, IL-8, and VEGFR production by cancer cells. Additionally, because ChemR23 is a member of the G-protein coupled class of receptors, agonist binding and activation of ChemR23 by a nonselective beta-adrenergic receptor blocker such as Timolol may result in adenylyl cyclase activation and a subsequent increase in cAMP. Thus, Resolvin E1 binding to β2-adrenergic receptors may result in receptor antagonism, further potentiating an inhibition of the release of IL-6, IL-8, and VEGF from cancer cells. This effect would be cumulative to the effects of Resolvin E1 binding and subsequent activation of receptor ChemR23 (e.g. a decrease in leukotriene B4 function, NF-kB activation, angiogenesis, and IL-12 production). Furthermore, Timolol binding to and activation of ChemR23 receptors may result in adenylyl cyclase activation and a subsequent reduction in the release of inflammatory and angiogenic mediators (e.g. leukotriene B4, NF-kB, and IL-12). This effect would also be cumulative to the effects of Timolol binding and inhibition of the β2-adrenergic receptor, including an inhibition in the release of IL-6, IL-8, and VEGF from cancer cells.

Another mechanism through which the administration of a non-selective beta-adrenergic receptor blocker may synergize with EPA:DHA:ASA metabolite formation to enhance anti-angiogenic and antioxidative processes is through mediation of COX-2 enzymatic activity. Because inflammation, which is often characteristic of angiogenic and oxidative processes, is a sequential process that ordinarily leads to its own resolution, inflammatory signals alternatively trigger the production of anti-inflammatory signals in a feed-back-loop fashion to restore tissue homeostasis. Such anti-inflammatory signals, including lipoxins and resolvins, may experience enhanced production as a result of the acetylation of COX-2 by ASA combined with high dosage EPA or DHA administration. However, recent studies have suggested that other pharmacological agents such as statins may initiate the formation of anti-inflammatory mediators, particularly 15-epi-Lipoxin A4, through COX-2 interaction (Birnbaum, Y., et al. 2006. Augmentation of myocardial production of 15-epi-lipoxin-A4 by pioglitazone and atorvastatin in the rat. Circulation 114:929-935). Particularly, research has shown that inducible nitric oxide synthase (iNOS) activates COX-2 through S-nitrosylation. As a result, Brinhaum et al. postulate that the administration of atorvastatin alters COX-2 through iNOS upregulation, producing the anti-inflammatory mediator 15-epi-LXA4 as result.

Followingly, many third generation beta-adrenergic receptor blockers have been shown to stimulate the release of nitric oxide from microvascular endothelial cells, likely through the upregulation of endothelial nitric oxide synthase (eNOS), resulting in blood-vessel dilatory effects characteristic of beta blocker administration (Kalinowski, M., et al. 2003. Third-Generation β-Blockers Stimulate Nitric Oxide Release From Endothelial Cells Through ATP Efflux. Circulation. 107: 2747-2752). Additionally, it has also been reported that in the delayed form of ischemic preconditioning (the cessation and commencement of tissue blood flow to minimize damage from final ischemic assault), the initial activation of eNOS leads to a rapid activation of both inducible nitric oxide synthase (iNOS) and COX-2 after a 24 hour period (Atar, S., et al. 2006. Atorvastatin-induced cardioprotection is mediated by increasing inducible nitric oxide synthase and consequent S-nitrosylation of cyclooxygenase-2. Am J Physiol Heart Circ Physiol. 290(5):H1960). Thus, in light of the hypoxic and ischemic environments experienced by microvascular tissues in exudative AMD and angiogenically-induced carcinogenesis, it is likely that a non-selective beta-adrenergic receptor blocker such as Timolol initially up regulates eNOS, leading to the immediate and subsequent activation of iNOS. Similar to statin administration, Timolol-induced activation of iNOS may lead to COX-2 activation through S-nitrosylation. Such activation, in combination with high dose antioxidant and EPA:DHA:ASA administration, may result in the enhanced production of anti-inflammatory mediators such as 15-epi-LXA4, well known for its inhibitory effects on neutrophil migration and infiltration, angiogenesis, NF-kB activation, and leukotriene B4 functionality.

Accordingly, the daily dosage of Timolol 0.5% comprising the preferred embodiment may be administered through topical application of at least one drop per eye twice per day for a minimum of thirty consecutive days.

Metformin

A generic medication that has recently garnered renewed interest as an anti-aging drug due to its newly found and wide-ranging efficacy is metformin. Originally approved by the FDA for the treatment of patients diagnosed with Type II diabetes mellitus, metformin is an oral antidiabetic drug of the biguanide class that has proven to be quite effective in decreasing blood glucose levels in diabetic patients primarily by inhibiting hepatic gluconeogenesis. Metformin is also indicated for the treatment of polycystic ovarian syndrome, a condition characterized by insulin resistance. The biguanide class of antidiabetic drugs are derived from the French lilac, a plant that has been used by certain indigenous populations for centuries to address excessive urination (a symptom of diabetes insipidus).

Molecularly, metformin activates a master metabolic regulator known as AMPK, a catabolic enzyme whose activation leads to increased glucose and fat metabolism as well as decreased hepatic glucose production. However, recent data has also shown that AMPK activation by metformin leads to the amelioration of conditions associated with cancer, diabetes, multiple sclerosis, epilepsy, and Huntington's disease. Such wide ranging effects are thought to result from the ensuing cascade that is ignited after AMPK activation (mimicking up- and down-regulation of genes and proteins observed with exercise and caloric restriction). AMPK activation has been shown to increase mitochondrial biogenesis and ATP generation, nuclear receptor activity (PPAR-gamma, RAR, VDR, TR), levels and activity of PGC-1alpha, antioxidant enzymes (MnSOD, Cu/ZnSOD, catalase, peroxiredoxin, thioredoxin), Nampt (increases NAD+ production), Sirtuins (NAD-dependent deacetylases), fatty acid beta-oxidation, Klotho gene (anti-aging gene that reduces inflammation) expression, mitochondrial transcription factor A, and FOXO3A.

Metformin has also been shown to downregulate proinflammatory mediators including IL-1beta, IL-6, IL-8, NF-kB and TNF-alpha. AMPK activation also leads to the inhibition of mTOR, a serine/threonine kinase whose upregulation has been implicated in the etiological pathology of diseases such as cancer, lupus, epilepsy, Alzheimer's disease, and inflammatory immune system activation. Metformin has recently been shown to selectively inhibit cancer stem cells through the inactivation of lin-28 (a miRNA associated with undifferentiated ESCs and cancer stem cells) by p53 upregulation via AMPK activation.

Recent research has also shown that AMPK activation via metformin, adiponectin (an adipokine induced by omega-3 fatty acid administration), or AICAR (an intermediate in the generation of inosine monophosphate) leads to positive regulation of hematopoietic, mesenchymal, neural, melanocyte, and retinal adult stem cells. For example, adiponectin has been shown to serve as a novel growth factor for HSCs (Di-Mascio L, et al. Identification of Adiponectin as a Novel Hemopoietic Stem Cell Growth Factor. The Journal of Immunology, 2007, 178: 3511-3520) and PPARgamma agonist administration (PPARgamma is upregulated by AMPK activation) leads to an accelerated recovery of bone marrow progenitor cells after 5-fluorouracil administration (Djazayeri K et al. Accelerated recovery of 5-fluorouracil-damaged bone marrow after rosiglitazone treatment. Eur J Pharmacol. 2005 Oct. 17; 522(1-3):122-9). Metformin also appears to enhance bone marrow progenitor cell differentiation through AMPK activation (Molinuevo M S, et al. Effect of metformin on bone marrow progenitor cell differentiation: in vivo and in vitro studies. J Bone Miner Res. 2010 February; 25(2): 211-21) while Lkb1, a metabolic sensor/kinase that is activated by sirtuins (SIRT3) and lies upstream of and activates AMPK, is necessary for hematopoietic stem cell survival (Gan B, et al. Lkb1 regulates quiescence and metabolic homeostasis of haematopoietic stem cells. Nature. 2010 Dec. 2; 468(7324):701-4). AMPK activation also results in the inhibition of mTOR hyperactivation, leading to decreased levels of ROS and mitigation of HSC exhaustion (Chen C, et al. The axis of mTOR-mitochondria-ROS and stemness of the hematopoietic stem cells. Cell Cycle. 2009 Apr. 15; 8(8): 1158-60). Hwang et al. also observed that metformin normalized cell proliferation and neuroblast differentiation in the dentate gyrus of Zucker diabetic fatty rats, while Bernardo et al. observed that PPARgamma agonists promoted the differentiation of oligodendrocyte progenitor cells into myelin-forming cells and upregulated their antioxidant defenses (catalase, CuZnSOD) (Hwang I K, et al. Metformin Normalizes Type 2 Diabetes-Induced Decrease in Cell Proliferation and Neuroblast Differentiation in the Rat Dentate Gyrus. Neurochem Res (2010) 35:645-650; Bernardo A, et al. Peroxisome proliferator-activated receptor-gamma agonists promote differentiation and antioxidant defenses of oligodendrocyte progenitor cells. J Neuropathol Exp Neurol. 2009 July; 68(7):797-808).

Research also indicates that rats fed resveratrol (a polyphenol found commonly found in muscadine grapes and a putative SIRT1 activator) experienced an increase in the proliferative state of neuronal stem cells in the hippocampus (Torres G, et al. Silent information regulator 1 mediates hippocampal plasticity through presenilin1. Neuroscience. 2011 Apr. 14; 179:32-40). AMPK activation leads to SIRT1 activation via upregulation of Nampt, which provides NAD+ as a substrate necessary for SIRT1 activation. Interestingly, the targeted deletion of PPARgamma in hair follicle stem cells of mice results in a condition that resembles primary cicatricial or "scarring" alopecia (PCA, characterized by proinflammatory lipid accumulation and infiltration of inflammatory cells) and patients diagnosed with lichen planopilaris (a form of PCA) show changes that exhibit a defect in peroxisomal biogenesis and lipid metabolism (Karnik P, et al. Hair follicle stem cell-specific PPARgamma deletion causes scarring alopecia. J Invest Dermatol. 2009 May; 129(5): 1243-57).

Accordingly, the daily dosage of metformin comprising the preferred embodiment may be administered through oral ingestion of at least one capsule containing 500 mg of metformin once per day for a minimum of thirty consecutive days.

N-Acetyl-L-Cysteine

Another medication that has garnered increasing interest due to efficacy observed in a wide-range of disorders is N-acetyl-L-cysteine (NAC). Although approved by the FDA as the only antidote for acetaminophen overdose, NAC is available without a prescription and is commonly sold in health store chains as a nutritional supplement. NAC is a derivative of acetylcysteine, which itself is derived from the amino acid L-cysteine (the nitrogen atom of the amino acid cysteine has an acetyl group attached to it). Due to its ability to break disulfide bonds in mucus and thus liquefy it, NAC has also proven useful as mucolytic agent or expectorant in patients with Cystic Fibrosis. However, the mechanism of action underlying NACs efficacy in such seemingly disparate diseases as multiple sclerosis and trichotillomania (compulsive hair pulling) is its ability to act as a precursor to glutathione synthesis.

Glutathione (GSH) is considered one of the most potent and important antioxidants within the cell, scavenging ROS such as peroxides and free radicals via the activity of its thiol or sulfhydryl group (—SH). Thiol groups are considered reducing agents by serving as electron donors to ROS, thus reducing disulfide bonds within cytoplasmic proteins to cysteines. In the process, GSH is itself converted to an oxidized and reactive form, GSSG, but is quickly converted back to its reduced form by glutathione reductase, which is constitutively active and inducible upon oxidative stress. Because healthy cells and tissues contain a glutathione pool that is more than 90% reduced, an increased ratio of oxidized (GSSG) to reduced (GSH) glutathione is an indicator of cellular toxicity and oxidative stress. In addition to acting directly to neutralize ROS, GSH is also capable of converting oxidized antioxidants such as vitamins E and C back to their reduced forms, dextoxifying xenobiotics (through the actions of glutathione-s-transferase), and regulating aspects of the immune system (e.g. antigen presentation and apoptosis).

Another intriguing effect of NAC administration is the inhibition RhoA. RhoA is a small GTPase that is activated by ROCK (a serine/threonine kinase that lies upstream of RhoA) and regulates the actin cytoskeleton. Numerous studies indicate that activation of RhoA (and thus ROCK) is associated with various neurological, autoimmune, and metabolic disorders, including Alzheimer's (RhoA activation in mouse models), CNS injury (RhoA inhibition lead to an enhancement of axon regeneration), diabetes (increased ROCK expression in mouse models), HIV (RhoA activation weakened the blood-brain-barrier), experimental autoimmune encephalomyelitis (RhoA+ cells found in rat brain), rheumatoid arthritis (RhoA activation in inflamed synovial membranes), cancer cell invasion (RhoA inhibition reduced cancer cell invasion by downregulating NF-kB), Huntington's disease (ROCK1 inhibition reduced mutant huntingtin aggregation), and erectile dysfunction (RhoA inhibition enhanced rat penile erections).

Other diseases that are associated with glutathione deficiency in which NAC proved efficacious include age-related macular degeneration (NAC suppressed choroidal neovascularization), cerebral palsy (attenuation of peroxisomal dysfunction and cerebral white matter injury by NAC), noiseinduced hearing loss (reduction of permanent threshold shifts and hair cell loss via NAC administration), and psoriasis (NAC attenuated TNF-alpha-induced production of cytokines in human keratinocytes).

Thus, it would appear that nearly every system in the body is affected by the efficiency (or lack thereof) of glutathione generation and activity, and similar to AMPK activation, adult stem/progenitor cells are not immune to the beneficial effects of efficient and robust levels of glutathione activity. For example, Gu et al. showed that mice with mutations in DKC1 (a gene encoding telomerase-associated protein dyskerin) exhibit growth defects, bone marrow failure, and excessive telomere shortening accompanied by increased DNA damage and ROS. NAC administration partially restored repopulation of hematopoietic stem cells within the bone marrow (Gu B W, et al. Accelerated hematopoietic stem cell aging in a mouse model of dyskeratosis congenita responds to antioxidant treatment. Aging Cell. 2011 April; 10(2):338-48). Muscari et al. showed that long-term treatment with NAC in aged rats protected mesenchymal stem cells from TNF-alpha-induced-death and also counteracted an excessive rate of MSC proliferation observed in control rats (Muscari C, et al. Long-term treatment with N-acetylcysteine, but not caloric restriction, protects mesenchymal stem cells of aged rats against tumor necrosis factor-induced death. Experimental Gerontology, Volume 41, Issue 8, August 2006, Pages 800-804). Kim et al. showed a significant decrease in neural stem cell proliferation and an increase in ROS formation and oxidative stress in an animal model of Ataxia-telangiectasia, characterized by a mutation in the ATM gene (responsible for DNA repair and redox homeostasis). The addition of NAC restored normal proliferation in Atm (−/−) stem cells and reduced the expression of the cell cycle inhibitors p27(kip1) and p21(cip1) (Kim J, et al. Loss of ATM impairs proliferation of neural stem cells through oxidative stress-mediated p38 MAPK signaling. Stem Cells. 2009 August; 27(8):1987-98). Research has also shown that that NAC and vitamin C co-administration enhances the capability of pancreatic stem/progenitor cells to undergo self-renewal and endocrine differentiation, while elevating the levels of glutathione via NAC administration in muscle-derived stem cells significantly enhances tissue regenerative capacity for cardiac repair after myocardial infarction (Linning K D, et al. Redox-mediated enrichment of self-renewing adult human pancreatic cells that possess endocrine differentiation potential. Pancreas. 2004 October; 29(3):e64-76; Drowley L, et al. Cellular Antioxidant Levels Influence Muscle Stem Cell Therapy. Molecular Therapy 18, 1865-1873).

Accordingly, the daily dosage of NAC comprising the preferred embodiment may be administered through oral ingestion of at least one capsule containing 600 mg of N-acetyl-L-cysteine twice per day for a minimum of thirty consecutive days.

Coenzyme Q10

Coenzyme Q10 (CoQ10), is an oil-soluble, vitamin-like substance that contains a quinone chemical group and ten isoprenyl chemical subunits it its tail. CoQ10 is found in abundance in various organs with high energy requirements (e.g. heart, kidney, liver) and is intimately involved in aerobic cellular respiration through the generation of adenosine triphosphate (ATP) via the electron transport chain (ETC) located within the inner mitochondrial membrane. CoQ10 has been shown to act as both an antioxidant and an electron carrier in the ETC due to its lipid solubility and its ability to exist in both fully reduced (ubquinol) and fully oxidized (ubqinone) forms.

The antioxidant properties of CoQ10 indicate that it may be efficacious in the treatment of many diseases or conditions associated with increased oxidative stress. The reduced form of CoQ10 gives up loosely held electrons quite easily, thereby facilitating its function as an antioxidant by preventing production of peroxy radicals, quenching perferryl radicals, regenerating vitamin E, preventing mitochondrial DNA oxidation, preventing initiation and propagation of lipid and protein oxidation, and preventing oxidation of low-density lipoprotiens.

In addition to its antioxidant properties, studies have shown that CoQ10 may prove effective in the treatment of liver fibrosis (suppression TGF-beta1 expression via Nrf2/ARE activation, upregulation of glutamate-cysteine ligase and glutathione S-transferase A2), atherosclerosis (prevention of LDL oxidation, increase in HDL and vitamin E, decrease in thiobarbituric acid reactive substances, malondialdehyde, and diene conjugates), hypertension (lowers systolic blood and diastolic blood without significant side-effects), cancer (decrease in ROS generation and MMP-2 activity), and obesity (decrease NADPH oxidase activity, decrease in CRP and STAMP2 levels).

Accordingly, the daily dosage of CoQ10 comprising the preferred embodiment may be administered through oral ingestion of at least one capsule containing 200 mg of once per day for a minimum of thirty consecutive days.

Melatonin

Also known chemically as N-acetyl-5-methoxytryptamine, melatonin is a naturally occurring compound found in plants, animals, and microbes and is a product of the amino acid tryptophan via hydroxylation and decarboxylation of tryptophan, forming 5-hydroxytryptamine (serotonin) as an intermediate. Although melatonin production is known to occur in the pineal gland and is photoperiod phase-dependent (i.e. decreased melatonin production upon exposure to light of appropriate wavelength and intensity and increased melatonin production during darkness), upon release into the into the blood stream, melatonin can readily traverse all morphophysiological barriers (e.g. placenta and blood brain barrier) and can thus enter every cell of the organism due to its amphiphilicity. Melatonin has also been observed to modify cell physiology via binding to the receptors MT1 and MT2, G protein-coupled receptors that are found in the brain and several peripheral organs. In the addition to the pineal gland, melatonin may also be synthesized in other mammalian tissues, including the retina, gut, bone marrow, and the lens of the eye.

Although many of the biological effects of melatonin are mediated by activation of melatonin receptors, melatonin has also proven to be an exceptionally powerful antioxidant, efficiently protecting mitochondrial and nuclear DNA from oxidation (Boutin J A, Audinot V, Ferry G, Delagrange P. Molecular tools to study melatonin pathways and actions. Trends Pharmacol Sci. 2005 August; 26(8):412-9). Melatonin, unlike other antioxidants such as vitamin C or vitamin E, does not undergo redox cycling and thus does not have the potential to act as a pro-oxidant, allowing melatonin to form stable-end products upon reacting with free radicals such as superoxide anion and hydroxyl radical (Poeggeler B, et al. Melatonin—a highly potent endogenous radical scavenger and electron donor: new aspects of the oxidation chemistry of this indole accessed in vitro. Ann NY Acad Sci. 1994 Nov. 17;

738:419-20). Interestingly, various metabolites that are produced in the melatonin antioxidant pathway (e.g. AFMK) act as antioxidants themselves, leading to the initiation of a free radical scavenging cascade upon melatonin metabolism, an attribute not shared by other convention antioxidants. Melatonin's antioxidant activities also extend to include the upregulation of enzymatic and non-enzymatic endogenous antioxidant enzymes, including Nrf2, glutathione, glutathione transferase, glutathione peroxidase, catalase, CuZn-SOD, and MnSOD. Consequently, conditions associated with reactive oxygen species overproduction in which melatonin has proven to be effective include hypoxic brain injury, brain cancer, and Parkinson's disease (Tütüncüler F, et al. The protective role of melatonin in experimental hypoxic brain damage. Pediatr Int. 2005 August; 47(4):434-9; Mao L, et al. Inhibition of breast cancer cell invasion by melatonin is mediated through regulation of the p38 mitogen-activated protein kinase signaling pathway. Breast Cancer Res. 2010; 12(6): R107; Singhal N K, et al. Melatonin or silymarin reduces maneb- and paraquat-induced Parkinson's disease phenotype in the mouse. J Pineal Res. 2011 March; 50(2):97-109.

In addition to its free radical scavenging activities, melatonin has also been shown to mitigate the effects of mediators involved in the activation of inflammatory processes. Although a variety of immune cells such as neutrophils, monocytes, macrophages, and eosinophils produce and release oxidants in response to pathogenic infections, exaggeration of the inflammatory response may lead to the upregulation of several genes involved inflammation, most notably NF-kB, known as a master regulator of the inflammatory response. NF-kB upregulation by reactive oxygen species leads to NF-kB translocation the nucleus, binding to DNA, and the upregulation of pro-inflammatory mediators, including TNF-alpha, iNOS, IL-2, and IL-6. Melatonin has been shown to reduce NF-kB binding to DNA, thus preventing production of pro-inflammatory cytokines, reducing leukocyte adhesion and migration, and reducing polymorphonuclear leukocyte recruitment to inflammatory sites (Chuang J I, et al. Effect of melatonin on NF-kappa-B DNA-binding activity in the rat spleen. Cell Biol Int. 1996 October; 20(10): 687-92; Sewerynek E, et al. Oxidative damage in the liver induced by ischemia-reperfusion: protection by melatonin. Hepatogastroenterology. 1996 July-August; 43(10):898-905.

Mounting evidence also indicates that melatonin serves as a positive regulator of mitochondrial bioenergetics. Melatonin is able to cross cell membranes and thus is taken up by and accumulates in mitochondria in a concentration-dependent manner. Within the mitochondria, melatonin has been shown to improve electron transport chain activity by stabilizing the inner mitochondrial membrane and increasing the activity of mitochondrial respiratory complexes I and IV in the liver and brain (cuña-Castroviejo D, Martín M, Macías M et al. Melatonin, mitochondria, and cellular bioenergetics. J Pineal Res 2001; 2:65-74; Martín M, Macías M, Escames G et al. Melatonin-induced increased activity of the respiratory chain complexes I and IV can prevent mitochondrial damage induced by ruthenium red in vivo. J Pineal Res 2000; 4:242-248). Research indicates that melatonin's upregulation of complexes I and IV may due to its direct interaction with complexes of the electron transport chain (ETC) and not via antioxidant activities (e.g. increasing electron flow by accepting and donating electrons within the ETC) (Tan D X, Manchester L C, Reiter R J et al. Melatonin directly scavenges hydrogen peroxide: a potentially new metabolic pathway of melatonin biotransformation. Free Radic Biol Med 2000; 11:1177-1185). Melatonin has also been shown to upregulate or preserve the expression of SIRT1, a histone deacetylase that significantly increases the rate of mitochondrial biogenesis (Cristòfol R, et al. Neurons from senescence-accelerated SAMP8 mice are protected against frailty by the sirtuin 1 promoting agents melatonin and resveratrol. J Pineal Res. 2012 April; 52(3):271-81.

Accordingly, the daily dosage of melatonin comprising the preferred embodiment may be administered through oral ingestion of at least one capsule containing 5 mg of melatonin once per day for a minimum of thirty consecutive days.

Magnesium

Magnesium (Mg), an alkaline earth metal with an oxidation number +2, is the fourth most common element found on earth and is vital to all living cells. Typically occurring as the $Mg^{2+}$ ion in biological systems, Mg is present in every cell type and is required as a cofactor by over 300 enzymes for proper catalytic function, including all enzymes that synthesize or utilize ATP (e.g. ATP must be complexed to magnesium in order to be biologically active). Mg is also important in maintaining the stability of polyphosphate compounds in cells that are associated with RNA and DNA synthesis (e.g. DNA ligase and DNA polymerase).

Several in vitro, animal model and human studies have demonstrated that Mg deficiency may lead to chronic inflammation, resulting in increased oxidative stress and a decrease in antioxidant defense (Weglicki W B, et al. Role of free radicals and substance P in magnesium deficiency. Cardiovasc Res 1996; 31:677-82; Mazur A, et al. Magnesium and the inflammatory response: potential physiopathological implications. Arch Biochem Biophys 2007; 458: 48-56). Mg deficiency has been shown to increase the production of superoxide anion, oxygen peroxide, and free radicals in several tissues (Hans C P, Chaudhary D P, Bansal D D. Effect of magnesium supplementation on oxidative stress in alloxanic diabetic rats. Magnes Res 2003; 16: 13-9; Yang Y, et al. Magnesium deficiency enhances hydrogen peroxide production and oxidative damage in chick embryo hepatocyte in vitro. Biometals 2006; 19:71-81) while also decreasing hepatic glutathione, vitamin E, and superoxide dismutase activity (Calviello G, et al. Mg deficiency induces mineral content changes and oxidative stress in rats. Biochem Mol Biol Int 1994; 32: 903-11). Diseases or conditions that are associated with increased oxidative stress in which Mg deficiency have been shown to be a contributing factor include diabetes, atherosclerosis, and metabolic syndrome (Barbagallo M, et al. Role of magnesium in insulin action, diabetes and cardiometabolic syndrome X. Mol Aspects Med 2003; 24: 39-52).

Mg deficiency has also been associated with a proinflammatory state by stimulating an overproduction and release of IL-1beta, IL-6, TNF-alpha, vascular cell adhesion molecule-1 (VCAM-1), and other markers of the inflammatory process (Kramer J H, et al. Dietary magnesium intake influences circulating pro-inflammatory neuropeptide levels and loss of myocardial tolerance to postischemic stress. Exp Biol Med 2003; 228: 665-73; Maier J A M, et al. Low magnesium promotes endothelial cell dysfunction: implications for atherosclerosis, inflammation and thrombosis. Biochim Biophys Acta 2004; 1689: 13-21). Human clinical data has also substantiated that deficiencies in dietary intake of Mg are associated with chronic low-grade systemic inflammation. For example, Song et al. noted that Mg levels were inversely correlated with the occurrence of metabolic syndrome and serum C-reactive protein (CRP, a measure of inflammation) while King et al. found that an elevated CRP level was positively associated with Mg intake below the Recommended Daily Allowance (Song Y, et al. Magnesium intake, C-reactive protein, and the prevalence of metabolic syndrome in middle-aged and older U.S. women, Diabetes Care 2005; 28: 1438-44; King D E, et al. Dietary magnesium and C-reactive protein levels. J Am Coll Nutr 2005; 24:166-71). Other diseases or conditions associated with chronic low-grade inflammation in which Mg deficiency has been shown to be a contributing factor include hypertension, osteoporosis, and asthma (Houston M. The role of magnesium in hypertension and cardiovascular disease. J Clin Hypertens (Greenwich). 2011 November; 13(11):843-7; Stendig-Lindberg G, et al. Prolonged magnesium deficiency causes osteoporosis in the rat. J Am Coll Nutr. 2004 December; 23(6):704S-11S; Kazaks A G, et al. Effect of oral magnesium supplementation on measures of airway resistance and subjective assessment of asthma control and quality of life in men and women with mild to moderate asthma: a randomized placebo controlled trial. J Asthma. 2010 February; 47(1):83-92).

Evidence also indicates that the role of Mg in energy metabolism extends beyond Mg's necessity for efficient ATP utilization (i.e. to be biologically active, ATP must be bound to Mg) to playing a vital mediator in mitochondrial respiration. For example, in addition to Mg functioning as a cofactor for the master metabolic kinases AMPK and LKB1, Ko et al. reported that Mg is required for the formation of the transition state in the ATP synthase reaction occurring in the F(1) catalytic sector of ATP synthase. Panov and Scarpa also noted that mitochondrial dehydrogenases such as alpha-ketoglutarate dehydrogenase complex, pyruvate dehydrogenase complex, and succinate dehydrogenase are either controlled by or sensitive to Mg concentrations within the mitochondria (Ko Y H et al. Chemical mechanism of ATP synthase. Magnesium plays a pivotal role in formation of the transition state where ATP is synthesized from ADP and inorganic phosphate. J Biol Chem. 1999 Oct. 8; 274(41):28853-6; Panov A, Scarpa A. Mg2+ control of respiration in isolated rat liver mitochondria. Biochemistry. 1996 Oct. 1; 35(39):12849-56). Moreover, because Mg bound to ATP is transported out of the mitochondria via the ATP-Mg/Pi carrier located on the inner mitochondrial membrane (IMM), depolarization of the IMM potential is necessary for the influx and efflux of ATP-Mg in exchange for inorganic phosphate (Pi). Certain neuronal pathologies such as migraine, Alzheimer's disease, and Parkinson's disease, are characterized by both dysfunctional mitochondrial membrane depolarization as well as disordered cellular Mg regulation (Boska M D, et al. Contrasts in cortical magnesium, phospholipid and energy metabolism between migraine syndromes. Neurology. 2002; 58:1227-1233; Andrasi E, et al. Brain aluminum, magnesium and phosphorus contents of control and Alzheimer-diseased patients. J Alzheimers Dis. 2005; 7:273-284; Yasui M, et al. Calcium, magnesium and aluminum concentrations in Parkinson's disease. Neurotoxicology. 1992; 13:593-600).

Accordingly, the daily dosage of magnesium comprising the preferred embodiment may be administered through oral ingestion of at least one capsule containing 250 mg of magnesium twice per day for a minimum of thirty consecutive days.

Curcumin

Curcumin, a curcuminoid derived from the Indian spice turmeric (Curcuma longa extract), containing 95 percent curcumin, is a natural phenol that can exist in various tautomeric forms, including two equivalent enol forms and a 1,3-diketo form. In the solid phase and in solution, the enol form has been shown to be more energetically stable. Curcumin has been shown in recent studies to exert a wide range of potential therapeutic or preventive effects in diseases associated with oxidative stress, inflammation, and metabolic dysregulation. Indeed, in vitro and animal studies have proven that curcumin displays antioxidant, anti-inflammatory, anti-viral, and anti-carcinogenic properties as well as stimulatory effects on mitochondrial biogenesis (e.g. inhibition of lipid peroxidation, oxidative DNA damage, NF-kB, TNF-alpha, and mTOR and upregulation MnSOD, CuZnSOD, Nrf2, BDNF, AMPK, and members of the Sirtuin class of histone deacetylases). Low dose curcumin administration has also been shown to enhance mouse adult hippocampal neurogenesis, as evidenced by a significant increase in the number of newly generated cells in the dentate gyrus of the hippocampus. Clinical trials are underway to study the effects of curcumin on diseases including Alzheimer's disease, myelodysplastic syndrome, colon cancer, pancreatic cancer, psoriasis, and HIV/AIDS.

Accordingly, curcumin may be added to the preferred embodiment of the present invention. The daily dosage of curcumin comprising the preferred embodiment may be administered through oral ingestion of at least one capsule containing 400 mg of curcumin once per day for a minimum of thirty consecutive days.

Green Tea Extract (Camellia sinensis)

Epigallocatechin 3-gallate (EGCG) is an ester of gallic acid and epigallocatechin and is the most abundant catechin found in green tea, but not black tea, due to the conversion of catechins to thearubigins and theaflavins during the production of black tea. EGCG has been shown in animal models and in vitro studies to possess antiviral, anticancer, antioxidant, anti-angiogenic, and anti-inflammatory effects. For example, research has shown that EGCG my attenuate adipoctye differentiation in 3T3 L-1 cells via AMPK activation and inhibit inflammatory mediators such as TNF-alpha in a murine model of human Sjogren's syndrome, an autoimmune disease (Hwang J T, et al. Genistein, EGCG, and capsaicin inhibit adipocyte differentiation process via activating AMP-activated protein kinase. Biochem Biophys Res Commun. 2005 Dec. 16; 338(2):694-9; Gillespie K, et al. Effects of oral consumption of the green tea polyphenol EGCG in a murine model for human Sjogren's syndrome, an autoimmune disease. Life Sci. 2008 Oct. 24; 83(17-18):581-8). EGCG has also been shown in cell models to inhibit HIV-1 infection by preventing the binding of HIV-1 glycoprotein (gp) 120 to the CD4 molecule on T cells and to slow cancer cell progression via inhibition of the anti-apoptotic protein Bcl-x1 (Williamson M P, et al. Epigallocatechin gallate, the main polyphenol in green tea, binds to the T-cell receptor, CD4: Potential for HIV-1 therapy. J Allergy Clin Immunol. 2006 December; 118(6): 1369-74; Leone M, et al. Cancer prevention by tea polyphenols is linked to their direct inhibition of antiapoptotic Bcl-2-family proteins. Cancer Res. 2003 Dec. 1; 63(23): 8118-21). Levels of heme oxygenase activity, mRNA levels, and protein expression as well as nuclear levels of Nrf2 (indicative of antioxidative activity) were also increased by EGCG administration, protecting rat neurons from hyperglycemia-induced oxidative stress (Na H K, et al. (−)-Epigallocatechin gallate induces Nrf2-mediated antioxidant enzyme expression via activation of PI3K and ERK in human mammary epithelial cells. Arch Biochem Biophys. 2008 Aug. 15; 476(2):171-7; Kesic M J, et al. Nrf2 expression modifies influenza A entry and replication in nasal epithelial cells. Free Radic Biol Med. 2011 Jul. 15; 51(2):444-53).

Accordingly, Green Tea Extract may be added to the preferred embodiment of the present invention. The daily dosage of Green Tea Extract (95% polyphenols, 80% catechins, 50% EGCG) comprising the preferred embodiment may be administered through oral ingestion of at least one capsule containing 100 mg of Green Tea Extract once per day for a minimum of thirty consecutive days.

Resveratrol

Resveratrol is a stillbenoid and phytoalexin produced by several plant species (particularly red grapes and Japanese knotweed) when under attack by pathogenic organisms such as fungi and or bacteria. Due to its potential effects on extending life span in model organisms such as *Drosophila melanogaster*, *Saccharomyces cerevisiae*, and *Caenorhabditis elegans*, resveratrol is currently the subject of numerous animal and human studies to determine its effects on age and non-age related diseases and conditions.

Resveratrol's mechanism of action is thought to primarily involve direct activation of SIRT1, a histone deacetylase of the Sirtuin class. Although questions remain as to whether resveratrol directly activates SIRT1 or AMPK (which in turn activates SIRT1), SIRT1 activation has been shown in cell cultures and animal models to mimic the biochemical effects of calorie restriction, including upregulation of PGC-1 alpha, MnSOD, FOXO3a, Nrf-2, glutathione, gamma-glutamylcysteine ligase, AMPK, and mitochondrial biogenesis. SIRT1 activation also leads to the downregulation of key inflammatory mediators including NF-kB, TNF-alpha, COX-2, IL-6, and iNOS. Numerous in vivo studies utilizing animal models demonstrate that resveratrol may prove to be therapeutically effective in the treatment or prevention of diseases including cancer (intestinal and colon carcinomas, esophageal tumors, and skin cancer), Alzheimer's disease (reduction of amyloid plaques), heart disease (inhibition of VCAM-1, platelet aggregation, LDL peroxidation, and stimulation of eNOS activity), diabetes (reduction of plasma glucose, increase in insulin sensitivity, and amelioration of polyphagia and polydipsia), and HIV/AIDS (reduction of Tat-induced HIV-1 LTR transactivation).

Accordingly, resveratrol may be added to the preferred embodiment of the present invention. The daily dosage of resveratrol comprising the preferred embodiment may be administered through oral ingestion of at least one capsule containing 125 mg of resveratrol once per day for a minimum of thirty consecutive days.

PQQ

Pyrroloquinoline quinone (PQQ), a redox cofactor found in enzymes known as quinoprotiens, has been shown to play an important nutritional role in mammals, serving as a cofactor in aminoadipate semialdehyde dehydrogenase (an enzyme that participates in lysine biosynthesis and degradation) and glucose dehydrogenase (an oxidoreductase that participates in the pentose phosphate pathway).

Several studies indicate that PQQ acts as a powerful antioxidant due to its exceptional molecular stability (allowing it to carry out thousands of electron transfers without undergoing biochemical breakdown) and its particular affinity for and effectiveness in neutralizing hydroxyl and superoxide radicals. In addition to protecting the mitochondria from oxidant-induced damage, PQQ has also been shown to be particularly adept at promoting spontaneous generation of new mitochondria in aging cells (i.e. mitochondrial biogenesis), likely through the upregulation of signaling molecules such as PGC-1 alpha, CREB, and DJ-1. PQQ has also been shown to provide neuroprotective effects (suppression of ROS, blocking of iNOS, upregulation of DJ-1, prevention of alpha-synuclein aggregation and formation of pathologic amyloid beta molecular structures), enhance cognitive function (acts synergistically with CoQ10 to enhance memory and attention), and promote cardioprotection (enhances left ventricle pumping pressure and reduces size of damaged infarct, reduces lipid peroxidation, and preserves and enhances cardiac mitochondrial function).

Accordingly, PQQ may be added to the preferred embodiment of the present invention. The daily dosage of PQQ comprising the preferred embodiment may be administered through oral ingestion of at least one capsule containing 10 mg of PQQ once per day for a minimum of thirty consecutive days.

Berberine

Berberine, found in plants such as *Berberis aqifolum* (Oregon grape), *Berberis aristata* (Tree Tumeric), and *Hydrastis canadensis* (Goldenseal), is a yellow-colored quaterneary ammonium salt from the protoberberine group of isoquinoline alkaloids. Well known within traditional Indian medicine for its medicinal properties, beberine has shown wide potential therapeutic properties, including anti-infective (i.e. *Candida albicans, Staphylococcus aureus*, and leishmaniasis), anti-inflammatory (suppression of proinflammatory cytokines, E-selectin, ICAM-1, NF-kB, TNF-alpha, iNOS, and COX-2), antioxidant (increases expression of HO-1, Nrf-2, catalase, superoxide dismutase, glutathione peroxidase, and glutathione), and mitochondrial biogenesis (increases expression of AMPK, SIRT1, NRF-1, and mtTFA).

The beneficial effects of beberine administration have been demonstrated in vitro, in vivo via animal models, and in human studies in various disease states including diabetes (enhancement of SOD activity, LDLR upregulation, decrease in insulin resistance, lowering of blood glucose comparable to metformin, and inhibition of dipeptidyl peptidase-4), hypercholesterolemia (lowers triglycerides, upregulation of LDLR mRNA expression, and AMPK activation), non-alcoholic fatty liver disease (prevention of hepatic stellate cell proliferation), cancer (inhibition of COX-2, TNF-alpha, ICAM-1, HIF-1, and IL-6), and Alzheimer's disease (inhibits cholinesterase and beta-amyloid pathways and antagonizes orexin receptors).

Accordingly, beberine may be added to the preferred embodiment of the present invention. The daily dosage of berberine comprising the preferred embodiment may be administered through oral ingestion of at least one capsule containing 200 mg of beberine once per day for a minimum of thirty consecutive days.

From the aforementioned description, it should be noted and appreciated that the present invention provides for novel methods and formulations for the treatment and/or prevention of diseases or conditions associated with oxidative stress, inflammation, and metabolic dysregulation. Although the present invention has been described in reference to specific embodiments, the written description and the embodiments described therein are illustrative and do not limit the present invention. Those skilled in the art may recognize modifications or variations to the present invention without departing from the underlying scope and spirit of the present invention.

What is claimed is:

1. A composition comprising on a daily dosage basis: approximately 1,200 milligrams (mg) vitamin C, approximately 360 International Units (IU) vitamin E, approximately 6,000 IU vitamin A, approximately 240 mg zinc, approximately 12 mg copper, approximately 330 mcg selenium, approximately 12 mg lutein, approximately 1,860 mg eicosapentaenoic acid (EPA), approximately 1,500 mg docosahexaenoic acid (DHA), approximately 650 mg acetylsalicylic acid (ASA), approximately 500 mg metformin, approximately 1,200 mg N-acetyl-L-cysteine, approximately 200 mg coenzyme Q10 (CoQ10), approximately 5 mg melatonin, and approximately 500 mg magnesium.

2. The composition of claim 1 wherein said vitamin C is provided in the form of ascorbic acid.

3. The composition of claim 1 wherein said vitamin E is provided in the form of dl-alpha tocopheryl acetate.

4. The composition of claim 1 wherein said zinc is provided in the form of zinc oxide.

5. The composition of claim 1 wherein said selenium is provided in the form of selenium selenate.

6. The composition of claim 1 wherein said copper is provided in the form of cupric oxide.

7. The composition of claim 1 wherein said eicosapentaenoic acid (EPA) is provided in the form of omega-3-acid ethyl esters.

8. The composition of claim 1 wherein said docosahexaenoic acid (DHA) is provided in the form of omega-3-acid ethyl esters.

9. The composition of claim 1 wherein said composition is supplemented with 100 milligrams (mg) *Camellia sinensis* (green tea extract); wherein said green tea extract is comprised of 95% polyphenols, 80% catechins; said polyphenols comprised of 50 percent epigallocatechin gallate; 400 milligrams *Curcuma longa* (turmeric) extract; wherein said turmeric extract is comprised of 95 percent curcumin; 125 mg resveratrol; 10 mg pyrroloquinoline quinone (PQQ); 200 mg berberine; or a combination thereof.

10. The composition of claim 1, wherein the composition is formulated as an oral dosage from the group consisting of: a caplet; capsule; or tablet.

11. A method of treating a human or other animal by administering a nutritional or dietary supplement composition comprising: approximately 1,200 milligrams (mg) vitamin C, approximately 360 International Units (IU) vitamin E, approximately 6,000 IU vitamin A, approximately 240 mg zinc, approximately 12 mg copper, 330 mcg selenium, approximately 12 mg lutein, approximately 1,860 mg eicosapentaenoic acid (EPA), approximately 1,500 mg docosahexaenoic acid (DHA), approximately 650 mg acetylsalicylic acid (ASA), approximately 500 mg metformin, approximately 1,200 mg N-acetyl-L-cysteine, approximately 200 mg coenzyme Q10 (CoQ10), approximately 5 mg melatonin, and approximately 500 mg magnesium.

12. The method of claim 11 wherein said vitamin C is provided in the form of ascorbic acid.

13. The method of claim 11 wherein said vitamin E is provided in the form of dl-alpha tocopheryl acetate.

14. The method of claim 11 wherein said zinc is provided in the form of zinc oxide.

15. The method of claim 11 wherein said selenium is provided in the form of selenium selenate.

16. The method of claim 11 wherein said copper is provided in the form of cupric oxide.

17. The method of claim 11 wherein said eicosapentaenoic acid (EPA) is provided in the form of omega-3-acid ethyl esters.

18. The method of claim 11 wherein said docosahexaenoic acid (DHA) is provided in the form of omega-3-acid ethyl esters.

19. The method of claim 11 wherein said composition is supplemented with 100 milligrams (mg) *Camellia sinensis* (green tea extract); wherein said green tea extract is comprised of 95% polyphenols, 80% catechins; said polyphenols comprised of 50 percent epigallocatechin gallate; 400 milligrams *Curcuma longa* (turmeric) extract; wherein said turmeric extract is comprised of 95 percent curcumin; 125 mg resveratrol; 10 mg pyrroloquinoline quinone (PQQ); 200 mg berberine; or a combination thereof.

20. The composition of claim 1 wherein the composition further comprises a pharmaceutical composition comprising timolol maleate at a concentration of 0.5% weight per volume (w/v) for topical ophthalmic application to the eye of a subject.

* * * * *